United States Patent
Boudon et al.

(10) Patent No.: US 10,470,991 B2
(45) Date of Patent: Nov. 12, 2019

(54) (R)-N-(ADAMANTYL-2-YL)PYRROLIDINE-2-CARBOXAMIDE DERIVATIVES FOR COSMETIC USE

(71) Applicant: DSM IP ASSETS B.V., Heerlen (NL)

(72) Inventors: Stephanie Boudon, Kaiseraugst (CH); Marc Heidl, Kaiseraugst (CH); Eileen Jackson, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/777,987

(22) PCT Filed: Dec. 9, 2016

(86) PCT No.: PCT/EP2016/080459
§ 371 (c)(1),
(2) Date: May 22, 2018

(87) PCT Pub. No.: WO2017/102587
PCT Pub. Date: Jun. 22, 2017

(65) Prior Publication Data
US 2018/0344604 A1    Dec. 6, 2018

(30) Foreign Application Priority Data

Dec. 14, 2015  (EP) .................................. 15199888
May 31, 2016  (EP) .................................. 16172141

(51) Int. Cl.
C07D 207/16    (2006.01)
A61K 8/49      (2006.01)
A61Q 19/08     (2006.01)
A61K 8/42      (2006.01)

(52) U.S. Cl.
CPC .............. *A61K 8/4913* (2013.01); *A61K 8/42* (2013.01); *A61K 8/492* (2013.01); *A61Q 19/08* (2013.01); *C07D 207/16* (2013.01)

(58) Field of Classification Search
CPC ........................ C07D 207/16; A61K 8/4913
See application file for complete search history.

(56) References Cited

U.S. PATENT DOCUMENTS

2005/0245533 A1    11/2005    Hoff et al.

FOREIGN PATENT DOCUMENTS

WO    2005/108359    11/2005
WO    2007/057768    5/2007

OTHER PUBLICATIONS

International Search Report for PCT/EP2016/080459, dated Mar. 9, 2017, 4 pages.
Written Opinion of the ISA for PCT/EP2016/080459, dated Mar. 9, 2017, 5 pages.
Tiganescu et al., "11β-Hydroxysteroid dehydrogenase blockade prevents age-induced skin structure and function defects", Journal of Clinical Investigation, vol. 123, No. 7, Jul. 1, 2013, pp. 3051-3060.
Su et al., "Adamantyl carboxamides and acetamides as potent human 11β-hydroxysteroid dehydrogenase type 1 inhibitors", Bioorganic & Medicinal Chemistry, vol. 20, No. 21, Sep. 12, 2012, pp. 6394-6402.

*Primary Examiner* — Karen Cheng
(74) *Attorney, Agent, or Firm* — Nixon & Vanderhye P.C.

(57) ABSTRACT

The present invention relates to novel selective 11-beta-hydroxysteroid dehydrogenase type 1 (11β-HSD1) inhibitors and the use thereof to prevent age-induced skin structure and function defects.

16 Claims, No Drawings

(R)-N-(ADAMANTYL-2-YL)PYRROLIDINE-2-CARBOXAMIDE DERIVATIVES FOR COSMETIC USE

This application is the U.S. national phase of International Application No. PCT/EP2016/080459 filed 9 Dec. 2016, which designated the U.S. and claims priority to EP Patent Application No. 15199888.7 filed 14 Dec. 2015, and EP Patent Application No. 16172141.0 filed 31 May 2016, the entire contents of each of which are hereby incorporated by reference.

The present invention relates to novel selective 11-beta-hydroxysteroid dehydrogenase type 1 (11β-HSD1) inhibitors and the use thereof to prevent age-induced skin structure and function defects.

Glucocorticoid (GC) excess adversely affects skin integrity, inducing thinning and impaired wound healing. Aged skin, such as in particular photo-exposed skin, shares a similar phenotype. Elevated 11β-HSD1 activity in aging skin leads to increased local GC generation, which may account for age-associated impairments in dermal integrity such as dermal and epidermal thinning, increased fragility of the skin, decrease of dermal collagen and increased trans-epidermal water loss. Furthermore, increased local GC concentration leads to poor wound healing [Tiganescu et al, J. Clin Invest. 2013; 123(7):3051-3060].

Thus, the topical administration of an effective amount of an 11β-HSD1 inhibitor is useful in the treatment of age-associated impairments in dermal integrity and wound healing. Long-term treatment with an 11β-HSD1 inhibitor is also useful in delaying the onset of ageing.

Surprisingly it has been found that compounds of formula (I) comprising a (R)—N-(adamantyl-2-yl)pyrrolidine-2-carboxamide residue

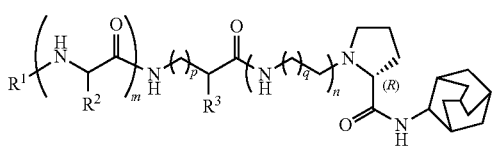

wherein n m and p are independently of each other 0 or 1, if n is 1, then q is 1 or 2, R$^1$ is selected from the group consisting of H, C$_1$-C$_6$acyl or hydroxyacetyl, R$^2$ is H or C$_1$-C$_6$alkyl, and R$^3$ is selected from the group consisting of H, C$_1$-C$_6$alkyl, arC$_1$-C$_6$alkyl, heteroarylC$_1$-C$_6$alkyl and biphenylC$_1$-C$_6$alkyl, wherein the aromatic aryl, heteroaryl or biphenyl residue may optionally be substituted, or a cosmetically acceptable salt thereof are highly efficient 11β-HSD1 inhibitors and thus particularly suitable for the incorporation into cosmetic compositions for the treatment of age-associated impairments in dermal integrity and wound healing.

The respective (S)-isomers as well as the respective 1-adamantyl-derivative show no or only a very limited activity.

Thus, in a first aspect, the present invention relates to a compound of formula (I)

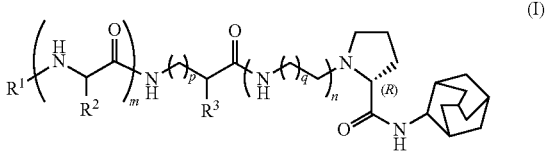

wherein n m and p are independently of each other 0 or 1, if n is 1, then q is 1 or 2, R$^1$ is selected from the group consisting of H, C$_1$-C$_6$acyl or hydroxyacetyl, R$^2$ is H or C$_1$-C$_6$alkyl, and R$^3$ is selected from the group consisting of H, C$_1$-C$_6$alkyl, arC$_1$-C$_6$alkyl, heteroarylC$_1$-C$_6$alkyl and biphenylC$_1$-C$_6$alkyl, wherein the aromatic aryl, heteroaryl or biphenyl residue may optionally be substituted, or a cosmetically acceptable salt thereof.

The aromatic aryl, heteroaryl and biphenyl residues in the arC$_1$-C$_6$alkyl, heteroarylC$_1$-C$_6$alkyl and biphenylC$_1$-C$_6$alkyl may be unsubstituted or substituted with one or more substituents. In all embodiments of the present invention, such substituents are preferably selected from halogen, hydroxy, nitro, cyano, C$_1$-C$_6$alkyl, C$_1$-C$_6$alkoxy and C$_1$-C$_6$alkanoyloxy. More preferably in all embodiments of the present invention the heteroaryl and the biphenyl residues are unsubstituted whereas the aryl residues are substituted with one substituent selected from the group consisting of F, Cl, hydroxy, cyano, C$_1$-C$_3$alkyl, C$_1$-C$_3$alkoxy and C$_1$-C$_3$alkanoyloxy, preferably from the group consisting of F, hydroxy, cyano, (m)ethoxy and acetoxy.

The term 'C$_1$-C$_6$alkyl' refers to unbranched C$_1$-C$_6$alkyl or branched C$_3$-C$_6$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups.

The term 'C$_1$-C$_6$acyl' refers to a —C(=O)C$_1$-C$_6$alkyl group such as acetyl, propionyl, n-butyryl, iso-butyryl, pentanoyl, hexanoyl and heptanoyl groups.

The term 'arC$_1$-C$_6$alkyl' refers to a —C$_1$-C$_6$alkyl-aryl wherein the term 'aryl' is e.g. a phenyl, indanyl or naphthyl group.

The term 'heteroarylC$_1$-C$_6$alkyl' refers to a —C$_1$-C$_6$alkyl-heteroaryl wherein the term "heteroaryl" refers to a 5- or 6-membered aromatic ring containing one or more heteroatoms, viz., N, O or S; these heteroaromatic rings may be fused to other aromatic systems.

The term 'biphenylC$_1$-C$_6$alkyl' refers to a —C$_1$-C$_6$alkyl-biphenyl wherein the term biphenyl refers to a 1,1'biphenyl which can be linked in o, m and p-position to the C$_1$-C$_6$alkyl residue.

The term 'C$_1$-C$_6$alkanoyloxyl' refers to a —OC(=O)C$_1$-C$_6$alkyl group such as acetyloxy, propionyloxy, n-butyryloxy, iso-butyryloxy, pentanoyloxy, hexanoyloxy and heptanoyloxy groups.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisomers.

The term 'or a cosmetically acceptable salt thereof' refers to compounds of formula (I) in the form of an acid addition salt such as in the form of a chloride, an acetate or a trifluoroacetate salt. Alternatively, the salt may be formed by reaction with an alkali or earth alkaline base resulting in the respective alkali or earth alkaline salt such as in particular the respective lithium, sodium, potassium, magnesium or calcium salts. Most preferred, in all embodiments of the present invention, are the compounds of formula (I) as such or in the form of their acetates or trifluoroacetates (i.e. as 2,2,2-trifluoroacetates). Such salts are easily prepared by a person skilled in the art.

In all embodiments of the present invention $R^1$ is preferably selected from the group consisting of H and $C_1$-$C_2$acyl, most preferably from H and acetyl.

In all embodiments of the present invention $R^2$ is preferably selected from the group consisting of is H and $C_1$-$C_2$alkyl, most preferably from H and methyl.

In all embodiments of the present invention $R^3$ is preferably selected from the group consisting of is H, $C_1$-$C_2$alkyl, ar$C_1$-$C_2$alkyl which may be substituted with one substituent selected from the group consisting of F, Cl, hydroxy, cyano, $C_1$-$C_3$alkyl, $C_1$-$C_3$alkoxy and $C_1$-$C_3$alkanoyloxy, preferably of F, hydroxy, cyano, (m)ethoxy and acetyloxy, an unsubstituted heteroaryl$C_1$-$C_2$alkyl and an unsubstituted biphenyl$C_1$-$C_2$alkyl. Most preferably in all embodiments of the present invention $R^3$ is selected from the group consisting of H, methyl, 3-hydroxybenzyl, 4-hydroxybenzyl, 4-methoxybenzyl, 4-ethoxybenzyl, 4-acetoxybenzyl, 4-fluorobenzyl, 2-cyanobenzyl, 4-cyanobenzyl, 1,1'-biphenyl-3-ylmethyl and 1H-indol-3-ylmethyl.

In a particular advantageous embodiment, the present invention relates to compounds of formula (I)
wherein n m and p are independently of each other 0 or 1
if n is 1, then q is 1,
$R^1$ is H or acetyl,
$R^2$ is H or methyl, and
$R^3$ is selected from the group consisting of H, methyl, 3-hydroxybenzyl,
4-hydroxybenzyl, 4-methoxybenzyl, 4-ethoxybenzyl, 4-acetoxybenzyl,
4-fluorobenzyl, 2-cyanobenzyl, 4-cyanobenzyl, 1H-indol-3-ylmethyl and
1,1'biphenyl-3-ylmethyl,
or a cosmetically acceptable salt thereof, such as preferably a trifluoroacetate.

In a very advantageous embodiment, the compounds of formula (I) are compounds of formula (II)

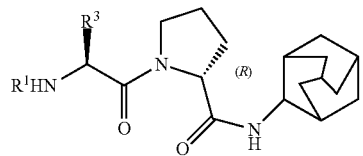

(II)

with all the definitions and preferences for $R^1$ and $R^3$ as outlined above.

Even more preferred are compounds of formula (II), wherein $R^1$ is H or acetyl and $R^3$ is selected from the group consisting of H, methyl, 3-hydroxybenzyl, 4-hydroxybenzyl, 4-methoxybenzyl, 4-ethoxybenzyl, 4-acetoxybenzyl, 4-fluorobenzyl, 2-cyanobenzyl, 4-cyanobenzyl, 1H-indol-3-ylmethyl and 1,1'biphenyl-3-ylmethyl or a cosmetically acceptable salt thereof such as preferably a trifluoroacetate.

In another very advantageous embodiment, the compounds of formula (I), are compounds of formula (III), more preferably of formula (IV)

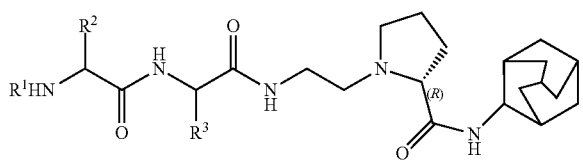

(III)

(IV)

with all the definitions and preferences as given above for $R^1$, $R^2$ and $R^3$.

Even more preferred are compounds of formula (III), such as in particular of formula (IV) wherein $R^1$ is H or acetyl, preferably H and $R^2$ and $R^3$ are independently of each other H or methyl or a cosmetically acceptable salt thereof such as preferably a trifluoroacetate.

Table 1 lists the most preferred compounds of formula (I) according to the present invention:

TABLE 1

| # | Structure | Compound of formula (I) with | Name |
|---|---|---|---|
| (I-a) | 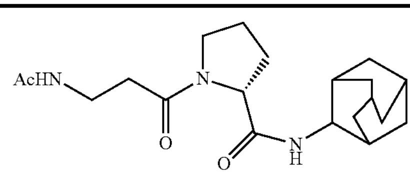 | n, m = 0<br>p = 1<br>$R^1$ = acetyl<br>$R^3$ = H | (R)-1-(3-acetamido-propanoyl)-N-(adamantan-2-yl)pyrrolidine-2-carboxamide |

TABLE 1-continued

| # | Structure | Compound of formula (I) with | Name |
|---|---|---|---|
| (I-b) | 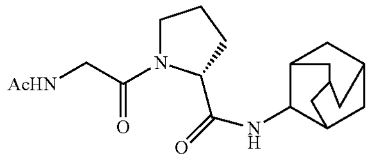 [SMILES: CC(=O)NCC(=O)N1CCC[C@@H]1C(=O)NC1C2CC3CC(C2)CC1C3] | n, m, p = 0<br>$R^1$ = acetyl<br>$R^3$ = H | (R)-1-(acetylglycyl)-N-(adamantan-2-yl)-pyrrolidine-2-carboxamide |
| (I-c) | 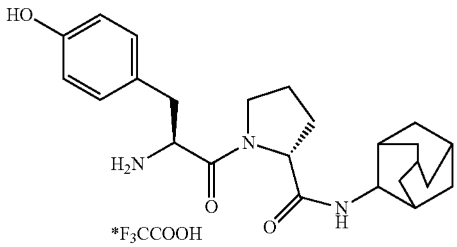 [SMILES: N[C@@H](Cc1ccc(O)cc1)C(=O)N1CCC[C@@H]1C(=O)NC1C2CC3CC(C2)CC1C3] | n, m, p = 0<br>$R^1$ = H<br>$R^3$ = 4-hydroxy-benzyl | (R)-1-(L-tyrosyl)-N-(adamantan-2-yl)-pyrrolidine-2-carboxamide trifluoroacetate |
| (I-d) | 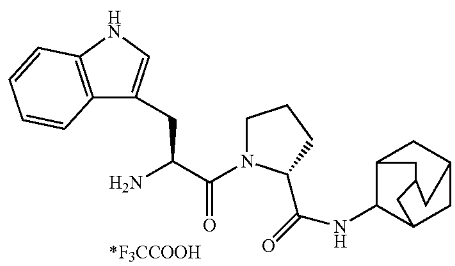 [SMILES: N[C@@H](Cc1c[nH]c2ccccc12)C(=O)N1CCC[C@@H]1C(=O)NC1C2CC3CC(C2)CC1C3] | n, m, p = 0<br>$R^1$ = H<br>$R^3$ = 1H-indol-3-ylmethyl | (R)-1-(L-tryptophyl)-N-(adamantan-2-yl)-pyrrolidine-2-carboxamide trifluoroacetate |
| (I-e) | 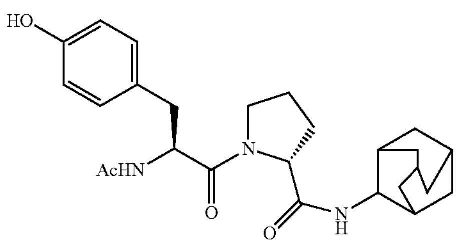 | n, m, p = 0<br>$R^1$ = acetyl<br>$R^3$ = 4-hydroxy-benzyl | (R)-1-(acetyl-L-tyrosyl)-N-(adamantan-2-yl)-pyrrolidine-2-carboxamide |
| (I-f) | 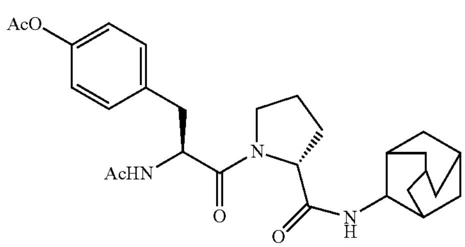 [SMILES: CC(=O)N[C@@H](Cc1ccc(OC(C)=O)cc1)C(=O)N1CCC[C@@H]1C(=O)NC1C2CC3CC(C2)CC1C3] | n, m, p = 0<br>$R^1$ = acetyl<br>$R^3$ = 4-acetoxy-benzyl | 4-((S)-2-acetamido-3-((R)-2-(adamantan-2-yl-carbamoyl)pyrrolidin-1-yl)-3-oxopropyl)phenyl acetate |
| (I-g) | 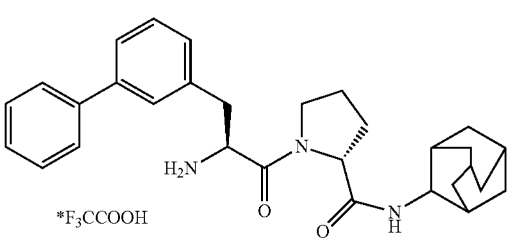 [SMILES: N[C@@H](Cc1cccc(-c2ccccc2)c1)C(=O)N1CCC[C@@H]1C(=O)NC1C2CC3CC(C2)CC1C3] | n, m, p = 0<br>$R^1$ = H<br>$R^3$ = 1,1'-biphenyl-3-ylmethyl | (R)-1-((S)-3-([1,1'-biphenyl]-3-yl)-2-aminopropanoyl)-N-(adamantan-2-yl)-pyrrolidine-2-carboxamide trifluoroacetate |

TABLE 1-continued

| # | Structure | Compound of formula (I) with | Name |
|---|---|---|---|
| (I-h) | 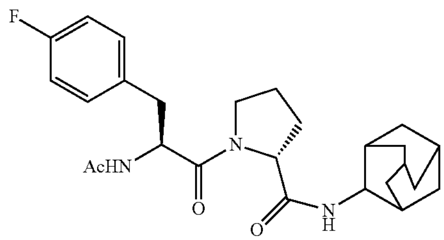 [SMILES: CC(=O)N[C@@H](Cc1ccc(F)cc1)C(=O)N1CCC[C@@H]1C(=O)NC1C2CC3CC(C2)CC1C3] | n, m, p = 0<br>$R^1$ = acetyl<br>$R^3$ = 4-fluorobenzyl | (R)-1-((S)-2-acetamido-3-(4-fluorophenyl)-propanoyl)-N-(adamantan-2-yl)-pyrrolidine-2-carboxamide |
| (I-i) | 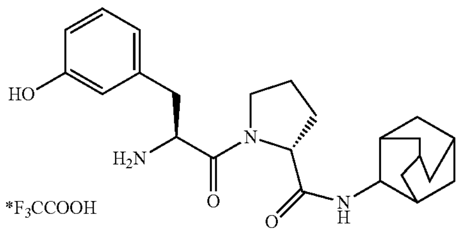 [SMILES: N[C@@H](Cc1cccc(O)c1)C(=O)N1CCC[C@@H]1C(=O)NC1C2CC3CC(C2)CC1C3] | n, m, p = 0<br>$R^1$ = H<br>$R^3$ = 3-hydroxy-benzyl | (R)-N-(adamantan-2-yl)-1-((S)-2-amino-3-(3-hydroxy-phenyl)propanoyl)pyrrolidine-2-carboxamide trifluoroacetate |
| (I-j) | 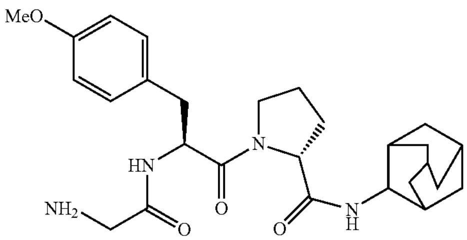 | n, p = 0<br>m = 1<br>$R^1$, $R^2$ = H<br>$R^3$ = 4-methoxy-benzyl | (R)-N-(adamantan-2-yl)-1-((S)-2-(2-aminoacetamido)-3-(4-methoxyphenyl)-propanoyl)pyrrolidine-2-carboxamide trifluoroacetate |
| (I-k) | 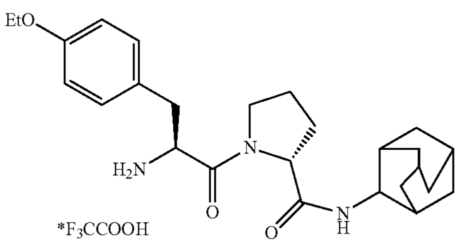 [SMILES: CCOc1ccc(C[C@H](N)C(=O)N2CCC[C@@H]2C(=O)NC2C3CC4CC(C3)CC2C4)cc1] | n, m, p = 0<br>$R^1$ = H<br>$R^3$ = 4-ethoxy-benzyl | (R)-N-(adamantan-2-yl)-1-((S)-2-amino-3-(4-ethoxy-phenyl)propanoyl) pyrrolidine-2-carboxamide trifluoroacetate |
| (I-l) | 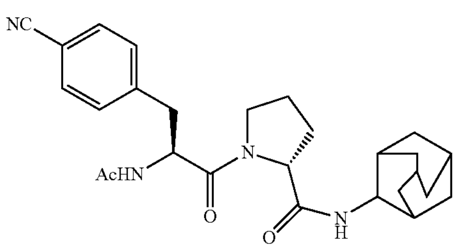 [SMILES: CC(=O)N[C@@H](Cc1ccc(C#N)cc1)C(=O)N1CCC[C@@H]1C(=O)NC1C2CC3CC(C2)CC1C3] | n, m, p = 0<br>$R^1$ = acetyl<br>$R^3$ = 4-cyanobenzyl | (R)-1-((S)-2-acetamido-3-(4-cyanophenyl)-propanoyl)-N-(adamantan-2-yl)pyrrolidine-2-carboxamide |
| (I-n) | 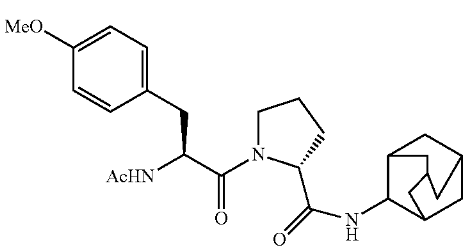 [SMILES: COc1ccc(C[C@H](NC(C)=O)C(=O)N2CCC[C@@H]2C(=O)NC2C3CC4CC(C3)CC2C4)cc1] | n, m, p = 0<br>$R^1$ = acetyl<br>$R^3$ = 4-methoxy-benzyl | (R)-1-((S)-2-acetamido-3-(4-methoxyphenyl)-propanoyl)-N-(adamantan-2-yl)pyrrolidine-2-carboxamide |

TABLE 1-continued

| # | Structure | Compound of formula (I) with | Name |
|---|---|---|---|
| (I-o) | 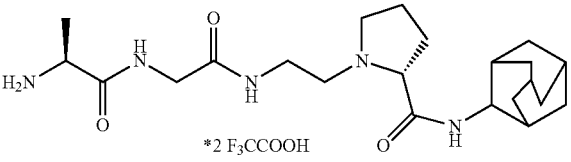 [SMILES: C[C@H](N)C(=O)NCC(=O)NCCN1CCC[C@@H]1C(=O)NC1C2CC3CC(C2)CC1C3] | n, m, q = 1<br>p = 0<br>$R^1$ = H<br>$R^2$ = methyl<br>$R^3$ = H | (R)-N-(adamantan-2-yl)-1-(2-(2-((S)-2-aminopropan-amido)acetamido)ethyl) pyrrolidine-2-carboxamide bistrifluoroacetate |
| (I-p) | 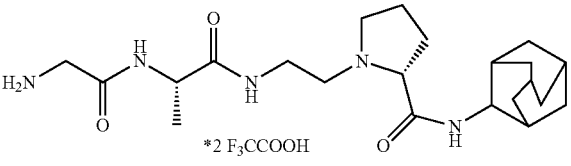 [SMILES: C[C@H](NC(=O)CN)C(=O)NCCN1CCC[C@@H]1C(=O)NC1C2CC3CC(C2)CC1C3] | n, m, q = 1<br>p = 0<br>$R^1$ = H<br>$R^2$ = H<br>$R^3$ = methyl | (R)-N-(adamantan-2-yl)-1-(2-((S)-2-(2-aminoacet-amido)propanamido) ethyl)pyrrolidine-2-carboxamide bistrifluoroacetate |
| (I-q) | 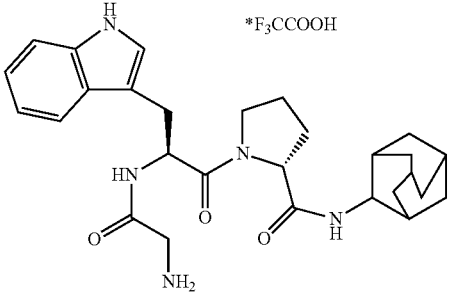 [SMILES: NCC(=O)N[C@@H](Cc1c[nH]c2ccccc12)C(=O)N1CCC[C@@H]1C(=O)NC1C2CC3CC(C2)CC1C3] | n, p = 0<br>m = 1<br>$R^1$, $R^2$ = H<br>$R^3$ = 1H-indol-3-ylmethyl | (R)-N-(adamantan-2-yl)-1-(glycyl)-L-tryptophyl)-pyrrolidine-2-carboxamide trifluoroacetate |
| (I-r) | 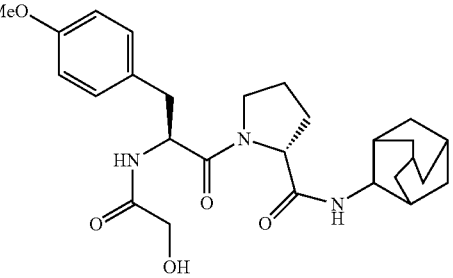 | n, m, p = 0<br>$R^1$ = hydroxyacetyl<br>$R^3$ = 4-methoxy-benzyl | (R)-N-(adamantan-2-yl)-1-((S)-2-(2-hydroxyacet-amido)-3-(4-methoxy-phenyl)propanoyl)-pyrrolidine-2-carboxmaide |
| (I-s) | 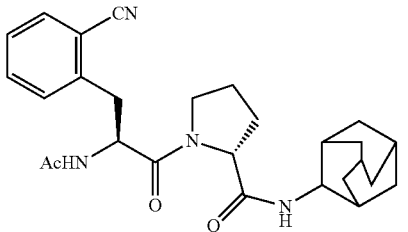 [SMILES: CC(=O)N[C@@H](Cc1ccccc1C#N)C(=O)N1CCC[C@@H]1C(=O)NC1C2CC3CC(C2)CC1C3] | n, m, p = 0<br>$R^1$ = acetyl<br>$R^3$ = 2-cyanobenzyl | R)-1-((S)-2-acetamido-3-(2-cyanophenyl)-propanoyl)-N-(adamantan-2-yl)pyrrolidine-2-carboxamide |

The compounds according to the present invention may be prepared from H-D-Pro-NH-2-Ad by methods standard in peptide chemistry as illustrated in the examples.

In yet another embodiment the present invention relates to the use of a compound of formula (I) with all the definitions and preferences as given herein as 11β-HSD1 inhibitor, in particular for the treatment of age-associated impairments in dermal integrity and wound healing and the symptoms associated herewith such as wrinkles and fine lines. Furthermore, the compounds of formula (I) are particularly suited to prevent (photo)age-induced skin structure and function defects such as skin thinning and wrinkle formation.

Thus, the invention also relates to a cosmetic composition comprising at least one compound of formula (I) and a cosmetically acceptable carrier.

The amount of the compound of formula (I) in the cosmetic composition can easily be adjusted by a person skilled in the art in order to achieve the desired beneficial effect. Preferably, the amount of the compound of formula (I) in the cosmetic compositions according to the present invention is at least 1 ppm based on the total weight of the cosmetic composition. In all embodiments of the present invention the amount of the compound of formula (I) is preferably selected in the range of about 0.00001 to 0.5 wt.-%, more preferably in the range of 0.0001 to 0.25 wt.-%, most preferably in the range of 0.0001 to 0.1 wt.-% based on the total weight of the cosmetic composition.

Furthermore, the invention also relates to a method to smoothen wrinkles and fine lines and/or to decrease their volume and depth, said method comprising the step of applying a cosmetic composition according to the present invention with all the definitions and preferences given herein to the affected area.

The term 'cosmetic composition' refers to compositions which are used to treat, care for or improve the appearance of the skin and/or the scalp. Particular advantageous cosmetic compositions are skin care compositions.

The cosmetic compositions according to the invention are preferably intended for topical application, which is to be understood as the external application to keratinous substances, such as in particular the skin.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skill in the art, and can include one or more compatible liquid or solid filler diluent, excipient, additive or vehicle which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and tonics. These product forms may be used for a number of applications, including, but not limited to, hand and body lotions, facial moisturizers, anti-ageing preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The cosmetic compositions according to the present invention can be prepared by conventional methods in the art such as e.g. by admixing a compound of formula (I) with all the definitions and preferences given herein with the cosmetically acceptable carrier. The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic compositions according to the invention may also comprise further cosmetically active ingredients conventionally used in cosmetic compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The cosmetic compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the cosmetic compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The amount of the cosmetic composition to be applied to the skin is not critical and can easily be adjusted by a person skilled in the art. Preferably the amount is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

Further suitable uses of the compounds according to the present invention encompass pharmaceutical applications. Thus, the compounds according to the present invention may be used to prepare a pharmaceutical composition for the treatment, prevention and/or prophylaxis of any disorder and disease where it is desirable to inhibit 11β-HSD1 in a patient in need thereof such as e.g. for the treatment, prevention and/or prophylaxis of conditions, disorders or diseases of the metabolic syndrome, insulin resistance, dyslipidemia, hypertension, obesity, type 2 diabetes, impaired glucose tolerance (IGT), impaired fasting glucose as well as diabetic complications including cardiovascular diseases, arteriosclerosis, atherosclerosis, neurodegenerative and psychiatric disorders. The compounds according to the present invention may also be useful to delay or prevent the progression from IGT to type 2 diabetes as well as metabolic syndrome into type 2 diabetes. The compounds may be applied topical, oral as well as parenteral without being limited thereto.

The invention is further illustrated with reference to the following, non-limiting examples, in which all percentages are by weight based on total weight unless otherwise specified.

EXPERIMENTAL PART

1. General Information
Abbreviations
AA Amino acid
Ad adamantyl
Boc tert-butyloxycarbonyl
DCM dichloromethane
DIPEA N,N-diisopropylethylamine
DMAP N,N-dimethylaminopyridine
DMF dimethylformamide
Fmoc fluorenylmethoxycarbonyl
HPLC High Pressure Liquid Chromatography
Pro proline
TFA trifluoroacetic acid
TBTU O-(Benzotriazol-1-yl)-N,N,N',N'-tetramethyluronium tetrafluoroborat Preparative HPLC purifications: performed on a Waters High Performance Liquid Chromatography LC-2525 equipped with a Waters 2767 Sample Manager and a Waters FCII automated fraction collector, using a Grom Saphir 110 C18 10 μm 50×300 mm$^2$ preparative column and a Waters 2487 double wavelength UV-Vis detector operating at 220 and 254 nm.

$H_2O$+0.07% TFA (A" phase) and MeCN+0.07% TFA (B" phase) were used as eluents, with a flow of 55 mL/min.

2. Synthetic Strategies
Synthesis of the Precursor: H-D-Pro-NH-2Ad *HCl

A suspension of 2.48 g (13.2 mmol, 1.1 eq) 2 adamantylamine hydrochloride is suspended in 15 ml DMF and 2.31 ml (13.2 mmol, 1.1 eq) DIPEA. 12 mmol of Boc-D-Pro-OH are dissolved in 15 ml DMF, then 3.85 g (12 mmol, 1 eq) TBTU and 6.9 ml (39.6 mmol, 3.3 eq) DIPEA were added. After 4 minutes, the pre-activated amino acid solution is added to the 2 adamantylamine hydrochloride suspension. After 60 minutes at room temperature, the reaction mixture is transferred into a separation funnel with ethyl acetate and water. The aqueous phase is re-extracted with ethyl acetate. The combined organic phases are washed with 5% $NaHCO_3$, 1M $KHSO_4$, and brine. The organic phase is dried over $Na_2SO_4$ and all volatile compounds are removed at 2 mbar/40° C. water bath. The residue is diluted in ethyl acetate and treated with 47 ml 2M HCl in diethylether and 66 ml 4M HCl in dioxane. The mixture is stirred overnight, concentrated in vacuum and diluted with 200 ml of diethylether. The precipitate is filtered and dried. Yield: 3.32 g (11.5 mmol, 96%).

Procedure 1: Ac-AA1-D-Pro-N H-2-Ad 214 mg (0.75 mmol, 1.0 eq) H-D-Pro-NH-2Ad *HCl obtained as outlined above is dissolved in 2.5 ml DMF and 0.13 ml (0.75 mmol, 1.0 eq) DIPEA. In a separate beaker the acetylated amino acid AA1 as indicated below is preactivated for 4 minutes by adding 277 mg (0.863 mmol, 1.15 eq) TBTU and 0.432 ml (2.475 mmol, 3.3 eq) DIPEA to a solution of 0.863 mmol (1.15 eq) Ac-AA1-OH in 2.5 ml DMF. The solutions are combined and allowed to react for one hour at room temperature. The reaction mixture is transferred into a separation funnel with ethyl acetate and water. The aqueous phase is re-extracted with ethyl acetate. The combined organic phases are washed with 5% $NaHCO_3$, 1M $KHSO_4$, and brine. The organic phase is dried over $Na_2SO_4$ and all volatile compounds are removed at 2 mbar/40° C. water bath. The respective crude products purified by preparative HPLC.

(I-a): AA1=Beta-alanine: 227 mg (0.62 mmol, 83%)
(I-b): AA1=Glycine: 211 mg (0.60 mmol, 80%)
Procedure 2a: H-AA2-D-Pro-NH-2-Ad*TFA 427 mg (1.5 mmol, 1.0 eq) H-D-Pro-NH-2Ad *HCl obtained as outlined above is dissolved in 5 ml DMF and 0.26 ml (1.5 mmol, 1.0 eq) DIPEA. In a separate beaker the Fmoc amino acid AA2 as indicated below is preactivated for 4 minutes by adding 1.15 eq TBTU and 3.3 eq DIPEA to a solution of 1.15 eq Fmoc-AA2-OH in 5 ml DMF. The solutions are combined and allowed to react for one hour at room temperature. The reaction mixture is transferred into a separation funnel with ethyl acetate and water. The aqueous phase is re-extracted with ethyl acetate. The combined organic phases are washed with 5% $NaHCO_3$, 1M $KHSO_4$, and brine. The organic phase is dried over $Na_2SO_4$ and all volatile compounds are removed at 2 mbar/40° C. water bath. The crude Fmoc-protected material is dissolved in 15 ml DCM and treated with 50 eq of diethylamine for 2 hours. The respective crude products are purified by preparative HPLC.

(I-c) AA2=L-Tyrosine: 311 mg (0.58 mmol, 39%)
(I-d): AA2=L-Tryptophane: 208 mg (0.37 mmol, 50%) (0.75 mmol scale)
Procedure 2b: H-AA2-D-Pro-NH-2-Ad*TFA The Boc amino acid AA2 as indicated below is preactivated by adding 1.0 eq TBTU and 3.3 eq DIPEA to a solution of 1.0 eq Boc-AA2-OH in 5 ml DMF. After 4 minutes, 0.542 mmol (1.0 eq) H-D-Pro-NH-2Ad *HCl is added. The mixture is allowed to react for one hour at room temperature. The reaction mixture is transferred into a separation funnel with ethyl acetate and water. The combined organic phases are washed with 5% $NaHCO_3$, 1M $KHSO_4$, and brine. The organic phase is dried over $Na_2SO_4$ and all volatile compounds are removed at 2 mbar/40° C. water bath. The crude Boc-protected material is dissolved in 20 ml/4M HCl in dioxane for 45 minutes. The crude product is purified by preparative H PLC.

(I-g): AA2 L-3-Phenyl-Phenylalanine: 221 mg (0.37 mmol, 72%)
(I-i): AA2=L-3-(3-Hydroxyphenyl)alanine: 85 mg (0.16 mmol, 32%)
(I-k): AA2=L-3-(4-Ethoxyphenyl)alanine: 246 mg (0.78 mmol, 78%) (1 mmol scale)
Procedure 2c: H—O-Methyl-Tyr-D-Pro-NH-2-Ad The L-Boc-O-Methyl-Tyrosine-OH is preactivated by adding 1.0 eq TBTU and 3.3 eq DIPEA to a solution of 1.0 eq Boc-AA2-OH in 5 ml DMF. After 4 minutes, 4.5 mmol (1.0 eq) H-D-Pro-NH-2Ad *HCl is added. The mixture is allowed to react for one hour at room temperature. The reaction mixture is transferred into a separation funnel with ethyl acetate and water. The combined organic phases are washed with 5% $NaHCO_3$, 1M $KHSO_4$, and brine. The organic phase is dried over $Na_2SO_4$ and all volatile compounds are removed at 2 mbar/40° C. water bath. The crude Boc-protected material is dissolved in 20 ml/4M HCl in dioxane for 45 minutes. The pH of the solution is adjusted to 8 by $NaHCO_3$, and the free base is extracted with ethyl acetate. The organic phase is dried over $Na_2SO_4$ and all volatile compounds are removed at 2 mbar/l 40° C. water bath. The intermediate is used without further purification in procedure 3 and 6.

(Intermediate 1): AA2=L-O-Methyl-Tyrosine 2105 mg (4.5 mmol, >99%)

Procedure 2d: H-AA2-D-Pro-NH-2-Ad *HCl

The Boc amino acid AA2 as indicated below is preactivated by adding 1.0 eq TBTU and 4 eq DIPEA to a solution of 1.0 eq Boc-4-Fluoro-Phe-OH in 5 ml DMF. After 4 minutes, 1.5 mmol (1.0 eq) H-D-Pro-NH-2Ad *HCl is added. The mixture is allowed to react for one hour at room temperature. The reaction mixture is transferred into a separation funnel with ethyl acetate and water. The combined organic phases are washed with 5% $NaHCO_3$, 1M KHSO4, and brine. The organic phase is dried over $Na_2SO_4$ and all volatile compounds are removed at 2 mbar/40° C. water bath. The crude Boc-protected material is dissolved in 25 ml/4M HCl in dioxane for 30 minutes. The hydrochloride is precipitated by adding 100 ml of diisopropylether, filtered off and dried.

(Intermediate 2): AA2=L-(4-fluoro-phenyl)alanine 573 mg (1.26 mmol, 84%)
(Intermediate 3): AA2=L-(2-Cyano-phenyl)alanine 443 mg (0.97 mmol, 97%) experiment performed at 1.0 mmol scale Procedure 3: Ac-AA2-D-Pro-NH-2-Ad 0.5 mmol (1.0 eq) H-AA2-D-Pro-NH-2-Ad from procedure 2a to 2d is suspended or dissolved in 2 ml DCM. A mixture of 47 microliters acetic anhydride, 47 microliters pyridine in 1 ml DCM is added. After 15 minutes, additional 47 microliters acetic anhydride, 47 microliters pyridine in 1 ml DCM is added. After 15 minutes, the reaction mixture is transferred into a separation funnel with ethyl acetate and 5% $NaHCO_3$. The organic phase is washed with 5% $NaHCO_3$, 1M $KHSO_4$, and brine. The organic phase is dried over $Na_2SO_4$ and all volatile compounds are removed at 2 mbar/40° C. water bath.

The crude product is purified by preparative HPLC.
(I-e): 142 mg (0.31 mmol, 63%)
(I-f): 41 mg (0.08 mmol, 16%)
(I-h): 317 mg (0.69 mmol, 55%)
(I-l): 246 mg (0.53 mmol, 43%) (experiment performed on 1.25 mmol scale)
(I-n): 408 mg (0.86 mmol, 57%) (experiment performed on 1.5 mmol scale)
(I-s): 321 mg (0.69 mmol, 69%) (experiment performed on 1.0 mmol scale)

Procedure 4: Gly-L-O-Methyl-Tyr-D-Pro-N H-2-Ad*TFA 0.75 mmol (1.0 eq) H—O-Methyl-Tyr-D-Pro-NH-2-Ad from procedure 2c is dissolved in DMF. 0.788 mmol (1.1 eq) Boc-Gly-OH is preactivated in DMF by adding 1.1 eq TBTU and 1.9 eq DIPEA. After 4 minutes, the solutions are combined and allowed to react for one hour at room temperature. The reaction mixture is transferred into a separation funnel with ethyl acetate and water. The aqueous phase is re-extracted with ethyl acetate. The combined organic phases are washed with 5% $NaHCO_3$, 1M $KHSO_4$, and brine. All volatile compounds are removed at 2 mbar/40° C. water bath. The crude Boc-protected material is dissolved in 10 ml 4M HCl in dioxane for 45 minutes. The crude product is purified by preparative HPLC.

(I-j): 276 mg (0.46 mmol, 61%)

Procedure 5: H-AA3-AA2-NH—(CH$_2$)$_2$-D-Pro-NH-2-Ad*TFA 4 mmol H-D-Pro-NH-2Ad *HCl prepared as outlined above is dissolved in 50 ml acetonitrile and 12 mmol of DIPEA. 6 mmol of tert-butyl (2-bromoethyl)carbamate were added and the mixture was stirred overnight. Additional 0.58 mmol of of tert-butyl (2-bromoethyl)carbamate were added and the mixture was stirred overnight. Additional 0.58 mmol of of tert-butyl (2-bromoethyl)carbamate were added and the mixture was stirred overnight. All volatile compounds are removed at 2 mbar 40° C. water bath and the residue is purified by preparative HPLC.

The crude Boc-NH—(CH$_2$)$_2$-D-Pro-NH-2-Ad is dissolved in 10 ml dioxane and 2 ml of TFA overnight. All volatile compounds are removed at 2 mbar/40° C. water bath. H$_2$N—(CH$_2$)$_2$-D-Pro-NH-2-Ad*TFA is dissolved in DMF and 2 eq DIPEA. 1.1 eq Boc-AA2-OH is preactivated in DMF by adding 1.1 eq TBTU and 3.3 eq DIPEA. After 4 minutes, the solutions are combined and allowed to react for one hour at room temperature. The reaction mixture is transferred into a separation funnel with ethyl acetate and water. The organic phase is washed with 5% NaHCO$_3$, 1M KHSO$_4$, and brine. All volatile compounds are removed at 2 mbar/40° C. water bath. The crude Boc-AA2-NH—(CH$_2$)$_2$-D-Pro-NH-2-Ad is dissolved in 15 ml 4M HCl in dioxane overnight. All volatile compounds are removed at 2 mbar/40° C. water bath. H-AA2-NH—(CH$_2$)$_2$-D-Pro-NH-2-Ad *HCl is dissolved in DMF and 2 eq DIPEA. 1.5 eq Boc AA3-OH is preactivated in DMF by adding 1.5 eq TBTU and 4.5 eq DIPEA. After 4 minutes, the solutions are combined and allowed to react for one hour at room temperature. All volatile compounds are removed at 2 mbar/40° C. water bath. The crude Boc-protected material is dissolved in 15 ml 4M HCl in dioxane overnight. The crude product is purified by preparative HPLC.

(I-o): 310 mg (0.47 mmol, 73%) (yield calculated for the four steps)

(I-p): 258 mg (0.38 mmol, 59%) (yield calculated for the four steps)

Procedure 6: hydroxyacetyl-L-O-Methyl-Tyr-D-Pro-NH-2-Ad 0.75 mmol (1.0 eq) H—O-Methyl-Tyr-D-Pro-NH-2-Ad from procedure 2c is dissolved in DMF. 0.788 mmol (1.1 eq) tBuO—Ac—OH is preactivated in DMF by adding 1.1 eq TBTU and 1.9 eq DIPEA. After 4 minutes, the solutions are combined and allowed to react for one hour at room temperature. The reaction mixture is transferred into a separation funnel with ethyl acetate and water. The aqueous phase is re-extracted with ethyl acetate. The combined organic phases are washed with 5% NaHCO$_3$, 1M KHSO$_4$, and brine. All volatile compounds are removed at 2 mbar/40° C. water bath. The crude Boc-protected material is dissolved in 10 ml 4M HCl in dioxane for 45 minutes and deprotected by adding 2×10 ml TFA and stirring overnight. The crude product is purified by preparative HPLC.

(I-r): 157 mg (0.32 mmol, 42%)

3. Activity Assays 3.1. Inhibition of 11-beta-hydroxysteroid Dehydrogenase Type 1

Preparation of Cell Lysates

Stably transfected human embryonic kidney (HEK-293) cells expressing 11β-HSD1 and hexose-6-phosphate dehydrogenase (the so called HHH7 clone) were cultivated for 48 h in Dulbecco's modified Eagle medium (DMEM) containing 4.5 g/L glucose, 10% fetal bovine serum, 100 U/mL penicillin, 0.1 mg/mL streptomycin, 1×MEM nonessential amino acids, and 10 mM HEPES buffer, pH 7.4. The cells were then washed with phosphate-buffered saline, and centrifuged for 4 min at 150×g. After removal of the supernatants, cell pellets were snap frozen on dry ice and stored at −80° C. until further use.

Activity Assay in Cell Lysates

Cell lysates were incubated for 10 min at 37° C. in TS2 buffer (100 mM NaCl, 1 mM EGTA, 1 mM EDTA, 1 mM MgCl$_2$, 250 mM sucrose, 20 mM Tris-HCl, pH 7.4) in a final volume of 22.2 μL containing either solvent (0.1% DMSO) or the inhibitor at the respective concentration as indicated in table 3-1. Enzyme activities were measured using the following conditions: 192 nM unlabeled cortisone, 8 nM radiolabeled cortisone, 450 μM NADPH.

Reactions were stopped after 10 min by adding an excess of unlabeled cortisone and cortisol (1:1, 2 mM, in methanol). The steroids were separated by TLC, using methanol-chloroform (1:9) as solvent, followed by scintillation counting and calculation of substrate concentration. Data were collected from four independent measurements (standard deviation<10%).

TABLE 3-1

Results of the enzyme assay

| # | Name | 11β-HSD1 Remaining activity [% of control] | |
|---|------|---|---|
| | | 1 μM | 300 nM |
| 1 | (R)-1-(3-acetamidopropanoyl)-N-(adamantan-2-yl)pyrrolidine-2-carboxamide (I-a) | 62 | na |
| 2 | (R)-1-(acetylglycyl)-N-(adamantan-2-yl)pyrrolidine-2-carboxamide (I-b) | 57 | na |
| 3 | (R)-1-(L-tyrosyl)-N-(adamantan-2-yl)pyrrolidine-2-carboxamide trifluoroacetate (I-c) | 45 | na |
| 4 | (R)-1-(L-tryptophyl)-N-(adamantan-2-yl)pyrrolidine-2-carboxamide trifluoroacetate (I-d) | 54 | na |
| 5 | (R)-1-(acetyl-L-tyrosyl)-N-(adamantan-2-yl)pyrrolidine-2-carboxamide(I-e) | 56 | na |
| 6 | 4-((S)-2-acetamido-3-((R)-2-(adamantan-2-ylcarbamoyl)pyrrolidin-1-yl)-3-oxopropyl)phenyl acetate (I-f) | 34 | na |
| 7 | (R)-1-((S)-3-([1,1'-biphenyl]-3-yl)-2-aminopropanoyl)-N-(adamantan-2-yl)pyrrolidine-2-carboxamide trifluoroacetate (I-g) | na | 48 |
| 8 | (R)-1-((S)-2-acetamido-3-(4-fluorophenyl)propanoyl)-N-(adamantan-2-yl)-pyrrolidine-2-carboxamide (I-h) | na | 37 |

TABLE 3-1-continued

Results of the enzyme assay

| # | Name | 11β-HSD1 Remaining activity [% of control] | |
|---|---|---|---|
| | | 1 μM | 300 nM |
| 9 | (R)-N-(adamantan-2-yl)-1-((S)-2-amino-3-(3-hydroxy-phenyl)propanoyl)pyrrolidine-2-carboxamide trifluoroacetate (I-i) | na | 61 |
| 10 | (R)-N-(adamantan-2-yl)-1-((S)-2-(2-aminoacetamido)-3-(4-methoxyphenyl)-propanoyl)pyrrolidine-2-carboxamide trifluoroacetate (I-j) | na | 49 |
| 11 | (R)-N-(adamantan-2-yl)-1-((S)-2-amino-3-(4-ethoxyphenyl)propanoyl)pyrrolidine-2-carboxamide trifluoroacetate (I-k) | na | 41 |
| 12 | (R)-1-((S)-2-acetamido-3-(4-cyanophenyl)-propanoyl)-N-(adamantan-2-yl)pyrrolidine-2-carboxamide (I-l) | na | 24 |
| 13 | (R)-1-((S)-2-acetamido-3-(4-methoxyphenyl)-propanoyl)-N-(adamantan-2-yl)pyrrolidine-2-carboxamide (I-n) | na | 65 |
| 14 | (R)-N-(adamantan-2-yl)-1-(2-(2-((S)-2-aminopropanamido)acetamido)ethyl)pyrrolidine-2-carboxamide bistrifluoroacetate (I-o) | na | 43 |
| 15 | (R)-N-(adamantan-2-yl)-1-(2-((S)-2-(2-aminoacetamido)propanamido)ethyl)pyrrolidine-2-carboxamide bistrifluoroacetate (I-p) | na | 57 |
| 16 | (R)-N-(adamantan-2-yl)-1-(glycyl-L-tryptophyl)pyrrolidine-2-carboxamide trifluoroacetate (I-q) | na | 69 |
| 17 | (R)-N-(adamantan-2-yl)-1-((S)-2-(2-hydroxyacet-amido)-3-(4-methoxy-phenyl)propanoyl)-pyrrolidine-2-carboxamide trifluoroacetate (I-r) | na | 72 |
| 18 | (R)-1-((S)-2-acetamido-3-(2-cyanophenyl)-propanoyl)-N-(adamantan-2-yl)pyrrolidine-2-carboxamide (I-s) | na | 77 | na = not analyzed 3.2. Human Keratinocytes Assay

Cell Culture: Primary human skin keratinocytes obtained from CellNTec advanced Cell Systems were maintained in CnT-PR medium at 37° C. in a humidified 5% $CO_2$-air atmosphere. Cells were subcultured before reaching confluence.

Assessment of 11β-HSD1 Activity: Human primary keratinocytes were pre-cultured in complete culture media (CnT-PR, CellNTec) to 90% of confluence. Subsequently cells were washed twice with PBS-buffer to remove remaining corticosteroids and media were exchanged to custom made hydrocortisone-free media. Cells were then treated with 1000 nM cortisone in combination with different concentrations of inhibitors as indicated in Table 3-2. 48 h later cell culture supernatant was collected and cortisol levels were assessed with the Cortisol Parameter Assay Kit (R&D Systems) following the instructions of the protocol and using a Multiskan Ascent plate reader (Labsystems).

Calculation: % remaining 11β-HSD1 activity=(cortisol-level with inhibitor/cortisol-level without inhibitor)*100%

TABLE 3-2

Results

| Compound | Concentration [nM] | remaining 11β-HSD1 activity [%] |
|---|---|---|
| Control | 0.00 | 100 |
| (I-l) | 3.16 | 94 |
| | 10.00 | 92 |
| | 31.62 | 76 |
| | 100.00 | 57 |
| | 316.20 | 28 |
| | 1000.00 | 12 |
| (I-h) | 3.16 | 100 |
| | 10.00 | 106 |
| | 31.62 | 89 |
| | 100.00 | 78 |
| | 316.20 | 52 |
| | 1000.00 | 25 |
| (I-k) | 3.16 | 95 |
| | 10.00 | 100 |
| | 31.62 | 89 |
| | 100.00 | 80 |
| | 316.20 | 58 |
| | 1000.00 | 36 |

3.3. Total Dermal Collagen after Cortisone and Cortisone/Inhibitor Treatment

Human skin from abdominal plastic surgery was used. The skin samples were cut in pieces of ~8×3 mm (Ø×thickness) and cultured up to day 6 in an air-liquid interface in a perforated ring of stainless steel in contact with a culture medium (modified Williams'E medium), while renewing the culture medium on day 3. Six skin specimens were used for each test sample. Each test sample (4 μl) was applied topically on top of each piece after cleaning of the surface with a cotton pad, which was subsequently covered with a 6 Ø mm delivery membrane, this procedure was repeated daily. After 6 days skin sections were stained with Picrosirius Red histochemical staining, that dyes collagen fibers in purple-red. The papillary dermis was selected for the analysis. The different colors of the pictures were separated by using a deconvolution matrix. After deconvolution only pink-reddish images are used. Within these images the evaluation of dermal collagen was performed by estimating both color intensity and distribution with IMAGE J (NIH) analysis software. Two slides of each skin sample were processed by image acquisition and related analysis (i.e. 12 images for each treatment).

TABLE 3-3

Results of the comparison treatments versus cortisone 0.1 μl at day 6

| # | Test sample compound | conc. (in DMSO) | Dermal collagen* | Increase versus cortisone (#2) |
|---|---|---|---|---|
| 1 | none (untreated) | 0 μM | 100% | — |
| 2 | cortisone° | 0.1 μM | 77% | — |
| 3 | (I-l) | 10 μM | 80% | +4% |
| 4 |  | 100 μM | 90% | +17% |
| 5 |  | 200 μM | 96% | +24% |

*Score of the dermal collagen of the untreated sample (#1) was set to 100%
°Positive control for collagen inhibition (−23% vs. untreated (#1))

As can be retrieved from the results outlined in Table 3-3, the 11β-HSD1 inhibitors according to the present invention counteracted cortisone activity by restoring total collagen in the papillary dermis.

4. References

As references 1-Adamantyl substituted compounds of formula 1 as outlined in table 4-1 have been prepared in analogy to the procedures outlined above and been tested in the enzyme assay. As can be retrieved from table 4-1, these compounds showed very little or no activity at all (at 1 μM concentration).

TABLE 4-1

Comparative data

| # | Name | 11β-HSD1 Remaining activity [% of control] 1 μM |
|---|---|---|
| R1 | (R)-1-(acetylglycyl)-N-((3S,5S,7S)-adamantan-1-yl)pyrrolidine-2-carboxamide | 100 |
| R2 | (R)-1-(3-acetamidopropanoyl)-N-((3S,5S,7S)-adamantan-1-yl)pyrrolidine-2-carboxamide | 91 |
| R3 | (R)-1-(L-tyrosyl)-N-((3S,5S,7S)-adamantan-1-yl)pyrrolidine-2-carboxamide 2,2,2-trifluoroacetate | 99 |
| R4 | (R)-1-(acetyl-L-tyrosyl)-N-((3S,5S,7S)-adamantan-1-yl)pyrrolidine-2-carboxamide | 98 |

5. Cosmetic Composition

Table 5-1 outlines exemplary O/W emulsions, wherein one compound selected from the group of (I-a) to (I-s) as outlined in table 1 (respectively table 3-1), is incorporated in the indicated amount.

TABLE 5-1

Exemplary O/W emulsion

| O/W Emulsions | 1 | 2 | 3 | 4 | 5 | 6 | 7 | 8 |
|---|---|---|---|---|---|---|---|---|
| Glyceryl Stearate | 2.5 | 2 | 1.2 | 1 |  |  | 1 | 1 |
| PEG-40 Stearate | 1 |  |  |  |  |  |  |  |
| PEG-100 Stearate |  | 2.5 |  |  |  |  |  | 1 |
| Ceteareth-20 |  |  |  |  | 1 |  |  |  |
| Glyceryl Stearate Citrate |  |  |  |  |  | 0.5 |  |  |
| Potassium Cetyl Phosphate |  |  |  |  |  |  | 3 | 1.5 |
| Stearic Acid |  |  | 2.5 | 3 |  |  |  |  |
| Cetearyl Alcohol | 4 |  |  | 2 |  |  | 2 |  |
| Stearyl Alcohol |  | 2 | 1 |  |  |  |  |  |
| Cetyl Alcohol |  |  | 1 | 1 |  |  |  | 0.5 |
| Acrylates/C$_{10-30}$ Alkyl Acrylate Crosspolymer |  |  |  | 0.2 | 0.2 | 0.4 |  | 0.2 |
| Carbomer | 0.1 |  | 0.2 |  |  |  |  |  |
| Xanthan Gum |  | 0.3 |  |  |  |  |  | 0.3 |
| C$_{12-15}$ Alkyl Benzoate | 5 |  |  | 2 | 5 | 5 | 10 | 5 |
| Petrolatum | 5 |  | 3 |  |  |  |  |  |
| Butylene Glycol Dicaprylate/Dicaprate |  | 4 | 2 |  | 9 |  |  | 9 |
| Hydrogenated Polydecene |  |  | 3 |  | 2 |  |  | 2 |
| Caprylic/Capric Triglyceride | 1 | 3 |  | 5 |  | 5 | 5 |  |
| Cyclomethicone |  | 5 | 2 |  |  | 10 |  |  |
| Methylpropanediol | 2 |  |  |  | 3 |  |  | 3 |
| Glycerine | 4 | 7 | 3 | 4 | 3 |  | 5 | 3 |
| Glyceryl Glucoside | 3.5 | 3 | 1 | 1 | 2 |  |  | 2 |
| Alcohol denat. | 1 | 3 | 0.5 | 10 | 4 | 8 |  | 4 |
| Butylene Glycol |  |  | 3 |  |  |  |  |  |
| Ascorbylglucoside |  | 0.5 |  | 1.0 |  | 1.5 |  | 0.1 |
| Ubiquinone (Coenzyme 10) | 0.1 |  | 0.05 |  |  |  | 0.01 |  |
| Hyaluronic acid |  |  |  |  | 0.2 |  |  |  |
| Bisabolol | 0.5 |  |  |  |  |  |  | 0.2 |
| Isotridecylsalicylate |  |  | 1 | 3 | 5 | 2 | 3 | 5 |
| Compound selected from the group of (I-a) to (I-s) | 0.001 | 0.25 | 0.0001 | 0.05 | 0.1 | 0.0003 | 0.03 | 0.002 |
| Dibutyl Adipate | 1.5 | 3 |  |  |  |  |  |  |
| Diisopropyl sebacate |  | 1 | 1 | 2 | 3 |  |  |  |
| Ethylhexyl Benzoate |  |  |  |  |  | 0.75 | 1.5 | 1 |
| Titanium Dioxide (PARSOL TX) |  |  | 0.5 | 2 |  |  |  |  |
| Methylene Bis-Benztriazoyl Tetramethylbutylphenol |  |  | 0.5 | 4 |  | 6 |  | 2 |
| Ethylhexyl methoxycinnamate |  |  |  |  | 2 |  |  |  |
| Phenylbenzimidazole Sulfonic Acid |  |  |  | 2 |  | 2 | 2 |  |
| Butyl Methoxydibenzoylmethane |  | 1 |  | 2 | 2 | 3 | 3 | 3 |

TABLE 5-1-continued

Exemplary O/W emulsion

| O/W Emulsions | 1 | 2 | 3 | 4 | 5 | 6 | 7 | 8 |
|---|---|---|---|---|---|---|---|---|
| Methylbenzylidene Camphor | | | | | 2 | 3 | | |
| Octocrylene | | 5 | | | | 2 | 10 | |
| Polysilicone-15 | | | | 2 | | 3 | | |
| Ethylhexyl Salicylate | | | | | 5 | | | |
| Homosalate | | | | 4 | | 2 | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | 4 | | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | | | | | q.s. | | | |
| Sodium Hydroxide | | | | | q.s. | | | |
| Water | | | | | Ad 100 | | | |

The invention claimed is:

1. A compound of formula (I) or a cosmetically acceptable salt thereof:

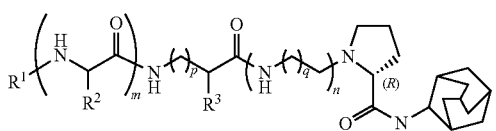

wherein n, m and p are independently of each other 0 or 1, wherein if n is 1, then q is 1 or 2,
R¹ is selected from the group consisting of H, $C_1$-$C_6$acyl and hydroxyacetyl,
R² is H or $C_1$-$C_6$alkyl, and
R³ is selected from the group consisting of H, $C_1$-$C_6$alkyl, ar$C_1$-$C_6$alkyl, heteroaryl$C_1$-$C_6$alkyl and biphenyl$C_1$-$C_6$alkyl, wherein the aromatic aryl, heteroaryl or biphenyl residue may optionally be substituted.

2. The compound according to claim 1, wherein the optionally substituted aromatic aryl, heteroaryl or biphenyl residue is substituted with a substituent selected from the group consisting of halogen, hydroxy, nitro, cyano, $C_1$-$C_6$alkyl, $C_1$-$C_6$alkoxy and $C_1$-$C_6$alkanoyloxy.

3. The compound according to claim 1, wherein the heteroaryl and biphenyl residues are unsubstituted and the aromatic aryl residue is substituted with one substituent selected from the group consisting of F, Cl, hydroxy, cyano, $C_1$-$C_3$alkyl, $C_1$-$C_3$alkoxy and $C_1$-$C_3$ alkanoyloxy.

4. The compound according to claim 1, wherein R¹ is selected from the group consisting of H and a $C_1$-$C_2$ acyl.

5. The compound according to claim 1, wherein R² is selected from the group consisting of is H and a $C_1$-$C_2$ alkyl.

6. The compound according to claim 1, wherein R³ is selected from the group consisting of is H, $C_1$-$C_2$alkyl, ar$C_1$-$C_2$alkyl, heteroaryl$C_1$-$C_2$alkyl and biphenyl$C_1$-$C_2$alkyl.

7. The compound according to claim 1, wherein R³ is selected from the group consisting of H, methyl, 3-hydroxybenzyl, 4-hydroxybenzyl, 4-methoxybenzyl, 4-ethoxybenzyl, 4-acetoxybenzyl, 4-fluorobenzyl, 2-cyanobenzyl, 4-cyanobenzyl, 1,1'-biphenyl-3-ylmethyl and 1 H-indo-3-ylmethyl.

8. The compound according to claim 1, wherein the cosmetically acceptable salt is an acetate or a trifluoroacetate.

9. The compound according to claim 1, wherein the compound is a compound of formula (II), (III) or (IV):

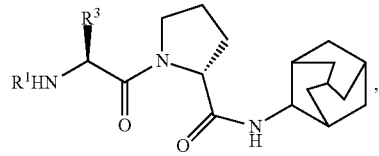

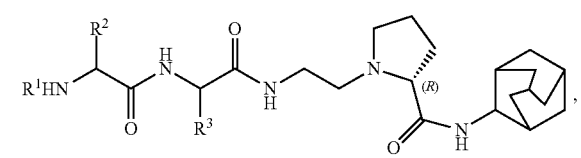

or

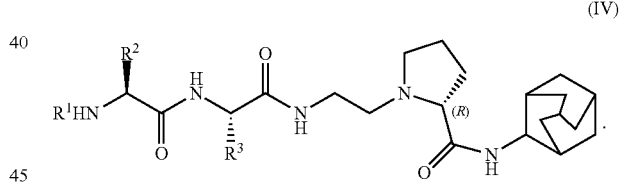

10. The compound according to claim 1, wherein the compound is:
(R)-1-(3-acetamidopropanoyl)-N-(adamantan-2-yl)pyrrolidine-2-carboxamide (I-a),
(R)-1-(acetylglycyl)-N-(adamantan-2-yl)pyrrolidine-2-carboxamide (I-b),
(R)-1-(L-tyrosyl)-N-(adamantan-2-yl)pyrrolidine-2-carboxamide trifluoroacetate (I-c),
(R)-1-(L-tryptophyl)-N-(adamantan-2-yl)pyrrolidine-2-carboxamide trifluoroacetate (I-d),
(R)-1-(acetyl-L-tyrosyl)-N-(adamantan-2-yl)pyrrolidine-2-carboxamide(I-e), 4-((S)-2-acetamido-3-((R)-2-(adamantan-2-ylcarbamoyl)pyrrolidin-1-yl)-3-oxopropyl) phenyl acetate (I-f),
(R)-1-((S)-3-([1,1'-biphenyl]-3-yl)-2-aminopropanoyl)-N-(adamantan-2-yl)pyrrolidine-2-carboxamide trifluoroacetate (I-g),
(R)-1-((S)-2-acetamido-3-(4-fluorophenyl)propanoyl)-N-(adamantan-2-yl)-pyrrolidine-2-carboxamide (I-h), (R)-N-(adamantan-2-yl)-1-((S)-2-amino-3-(3-hydroxyphenyl)propanoyl)pyrrolidine-2-carboxamide trifluoroacetate (I-i), (R)-N-(adamantan-2-yl)-1 -((S)-2-(2-aminoacetamido)-3-(4-methoxyphenyl)-propanoyl)pyrrolidine-2-carboxamide trifluoroacetate (I-j), (R)-N-(adamantan-2-yl)-1-((S)-2-amino-3-(4-ethoxyphenyl)propanoyl)pyrrolidine-2-carboxamide trifluoroacetate (I-k), (R)-1 -((S)-2-acetamido-3-(4-cyanophenyl)-propanoyl)-N-(adamantan-2-yl)pyrrolidine-2-carboxamide (I-l), (R)-1 -((S)-2-acetamido-3-(4-methoxyphenyl)-propanoyl)-N-(adamantan-2-yl)pyrrolidine-2-carboxamide (I-n), (R)-N-(adamantan-2-yl)-1 -(2-(2-((S)-2-aminopropanamido)acetamido)ethyl)pyrrolidine-2-carboxamide bistrifluoroacetate (I-o), (R)-N-(adamantan-2-yl)-1 -(2-((S)-2-(2-aminoacetamido)propanamido)ethyl)pyrrolidine-2-carboxamide bistrifluoroacetate (I-p), (R)-N-(adamantan-2-yl)-1 -(glycyl-L-tryptophyl)pyrrolidine-2-carboxamide trifluoroacetate (I-q), (R)-N-(adamantan-2-yl)-1 -((S)-2-(2-hydroxyacetamido)-3-(4-methoxy-phenyl)propanoyl)-pyrrolidine-2-carboxamide trifluoroacetate (I-r), or (R)-1 -((S)-2-acetamido-3-(2-cyanophenyl)-propanoyl)-N-(adamantan-2-yl)pyrrolidine-2-carboxamide (I-s).

11. The compound according to claim 3, wherein the aromatic aryl residue is substituted with one substituent selected from the group consisting of F, hydroxy, cyano, methoxy, ethoxy and acetoxy.

12. A cosmetic composition comprising at least one compound according to claim 1 and a cosmetically acceptable carrier.

13. The cosmetic composition according to claim 12, wherein the at least one compound of formula (I) is present in an amount, based on total weight of the cosmetic composition, within a range of about 0.00001 to 0.5 wt.-%.

14. A method to smoothen wrinkles and fine lines of skin and/ or to decrease volume and depth thereof, wherein the method comprises the step of applying an effective amount of the cosmetic composition according to claim 12 to an area of skin affected by wrinkles and fine lines.

15. A method of inhibiting 11 β-HSD1 in skin which comprises applying to skin an amount effective to inhibit 11 β-HSD1 of a compound of formula (I) or a cosmetically acceptable salt thereof:

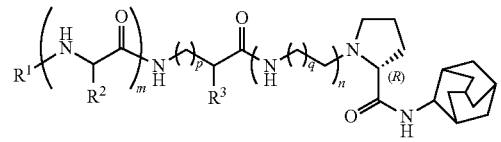

(I)

wherein n, m and p are independently of each other 0 or 1, and if n is 1, then q is 1 or 2, $R^1$ is selected from the group consisting of H, $C_1$-$C_6$acyl or hydroxyacetyl, $R^2$ is H or $C_1$-$C_6$alkyl, and $R^3$ is selected from the group consisting of H, $C_1$-$C_6$alkyl, ar$C_1$-$C_6$alkyl, heteroaryl$C_1$-$C_6$alkyl and biphenyl$C_1$-$C_6$alkyl, wherein the aromatic aryl, heteroaryl or biphenyl residue may optionally be substituted.

16. A method of cosmetically treating (photo)age-induced skin structure and function defects which comprises applying an effective amount of a compound of formula (I) or a cosmetically acceptable salt thereof onto skin in need of treatment for (photo)age-induced skin structure and function defects:

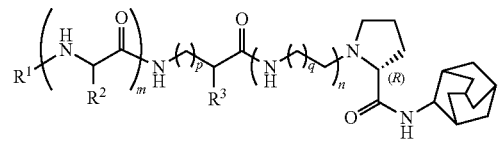

(I)

wherein n, m and p are independently of each other 0 or 1, and if n is 1, then q is 1 or 2, $R^1$ is selected from the group consisting of H, $C_1$-$C_6$acyl or hydroxyacetyl, $R^2$ is H or $C_1$-$C_6$alkyl, and $R^3$ is selected from the group consisting of H, $C_1$-$C_6$alkyl, ar$C_1$-$C_6$alkyl, heteroaryl$C_1$-$C_6$alkyl and biphenyl$C_1$-$C_6$alkyl, wherein the aromatic aryl, heteroaryl or biphenyl residue may optionally be substituted.

\* \* \* \* \*